(12) United States Patent
Mohanasundaram

(10) Patent No.: US 11,717,312 B2
(45) Date of Patent: Aug. 8, 2023

(54) SURGICAL SYSTEM INCLUDING BLADE VISUALIZATION MARKINGS

(71) Applicant: Covidien LP, Mansfield, MA (US)

(72) Inventor: Suresh Kumar Prema Mohanasundaram, Chennai (IN)

(73) Assignee: Covidien LP, Mansfield, MA (US)

( * ) Notice: Subject to any disclaimer, the term of this patent is extended or adjusted under 35 U.S.C. 154(b) by 111 days.

(21) Appl. No.: 17/491,567

(22) Filed: Oct. 1, 2021

(65) Prior Publication Data

US 2023/0107765 A1 Apr. 6, 2023

(51) Int. Cl.
*A61B 17/32* (2006.01)
*A61B 18/14* (2006.01)
*A61B 90/00* (2016.01)

(52) U.S. Cl.
CPC .. *A61B 17/320092* (2013.01); *A61B 18/1445* (2013.01); *A61B 2017/320074* (2017.08); *A61B 2017/320094* (2017.08); *A61B 2018/1452* (2013.01); *A61B 2090/0811* (2016.02)

(58) Field of Classification Search
CPC . A61B 17/28; A61B 17/29; A61B 17/320092; A61B 2017/320094; A61B 2017/320074; A61B 18/1445; A61B 2018/1452; A61B 2090/0811
See application file for complete search history.

(56) References Cited

U.S. PATENT DOCUMENTS

| | | |
|---|---|---|
| 1,813,902 A | 7/1931 | Bovie |
| 2,235,274 A | 3/1941 | Trehern |
| 2,874,470 A | 2/1959 | Richards |
| 2,990,616 A | 7/1961 | Balamuth |
| 3,432,691 A | 3/1969 | Shoh |
| 3,489,930 A | 1/1970 | Shoh |
| 3,526,792 A | 9/1970 | Shoh |
| 3,629,726 A | 12/1971 | Popescu |
| 3,668,486 A | 6/1972 | Silver |
| 3,809,977 A | 5/1974 | Balamuth et al. |
| 3,875,945 A | 4/1975 | Friedman |
| 3,924,335 A | 12/1975 | Balamuth et al. |
| 4,012,647 A | 3/1977 | Balamuth et al. |
| 4,193,818 A | 3/1980 | Young et al. |
| 4,227,110 A | 10/1980 | Douglas et al. |
| 4,300,083 A | 11/1981 | Heiges |
| 4,302,728 A | 11/1981 | Nakamura |
| 4,370,302 A | 1/1983 | Suzuoka et al. |
| 4,641,053 A | 2/1987 | Takeda |
| 5,113,116 A | 5/1992 | Wilson |
| 5,224,680 A | 7/1993 | Greenstein et al. |

(Continued)

*Primary Examiner* — Ashley L Fishback
(74) *Attorney, Agent, or Firm* — Carter, DeLuca & Farrell LLP

(57) ABSTRACT

An end effector assembly of a surgical system includes a blade and a jaw member movable relative to the blade between a spaced-apart position and an approximated position for clamping tissue. The blade defines a first width and the jaw member defines a second width wider than the first width. The jaw member defines a first side facing the blade and a second side facing away from the blade. A marking is formed on the second side of the jaw member facing away from the blade. The marking defines a third width substantially equal to the first width of the blade to allow a surgeon to visualize a width of the blade when the blade is not visible.

14 Claims, 6 Drawing Sheets

(56) References Cited

U.S. PATENT DOCUMENTS

| | | |
|---|---|---|
| 5,264,925 A | 11/1993 | Shipp et al. |
| 5,275,166 A | 1/1994 | Vaitekunas et al. |
| 5,374,813 A | 12/1994 | Shipp |
| 5,394,187 A | 2/1995 | Shipp |
| 5,408,268 A | 4/1995 | Shipp |
| 5,451,220 A | 9/1995 | Ciervo |
| 5,490,860 A | 2/1996 | Middle et al. |
| 5,565,520 A | 10/1996 | Fock et al. |
| 5,582,617 A | 12/1996 | Klieman et al. |
| 5,593,414 A | 1/1997 | Shipp et al. |
| 5,685,311 A | 11/1997 | Hara |
| 5,717,306 A | 2/1998 | Shipp |
| 5,728,130 A | 3/1998 | Ishikawa et al. |
| 5,776,155 A | 7/1998 | Beaupre et al. |
| 5,792,138 A | 8/1998 | Shipp |
| 5,796,056 A | 8/1998 | Bredow et al. |
| 5,810,859 A | 9/1998 | DiMatteo et al. |
| 5,858,018 A | 1/1999 | Shipp et al. |
| 5,873,873 A | 2/1999 | Smith et al. |
| 5,897,569 A | 4/1999 | Kellogg et al. |
| 5,910,152 A | 6/1999 | Bays |
| 5,938,633 A | 8/1999 | Beaupre |
| 5,944,737 A | 8/1999 | Tsonton et al. |
| 5,947,984 A | 9/1999 | Whipple |
| 5,954,736 A | 9/1999 | Bishop et al. |
| 5,993,465 A | 11/1999 | Shipp et al. |
| 5,994,855 A | 11/1999 | Lundell et al. |
| 6,031,526 A | 2/2000 | Shipp |
| 6,036,667 A | 3/2000 | Manna et al. |
| 6,068,647 A | 5/2000 | Witt et al. |
| 6,095,981 A | 8/2000 | McGahan |
| 6,162,194 A | 12/2000 | Shipp |
| 6,183,426 B1 | 2/2001 | Akisada et al. |
| 6,220,098 B1 | 4/2001 | Johnson et al. |
| 6,254,623 B1 | 7/2001 | Haibel, Jr. et al. |
| 6,257,241 B1 | 7/2001 | Wampler |
| 6,278,218 B1 | 8/2001 | Madan et al. |
| 6,280,407 B1 | 8/2001 | Manna et al. |
| 6,283,981 B1 | 9/2001 | Beaupre |
| 6,284,185 B1 | 9/2001 | Tokuda et al. |
| 6,287,344 B1 | 9/2001 | Wampler et al. |
| 6,290,575 B1 | 9/2001 | Shipp |
| 6,306,157 B1 | 10/2001 | Shchervinsky |
| 6,309,400 B2 | 10/2001 | Beaupre |
| 6,325,811 B1 | 12/2001 | Messerly |
| 6,328,751 B1 | 12/2001 | Beaupre |
| 6,350,269 B1 | 2/2002 | Shipp et al. |
| 6,352,532 B1 | 3/2002 | Kramer et al. |
| 6,416,486 B1 | 7/2002 | Wampler |
| 6,423,082 B1 | 7/2002 | Houser et al. |
| 6,432,118 B1 | 8/2002 | Messerly |
| 6,443,968 B1 | 9/2002 | Holthaus et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,142 B1 | 10/2002 | Faller et al. |
| 6,480,796 B2 | 11/2002 | Wiener |
| 6,482,220 B1 | 11/2002 | Mueller |
| 6,491,708 B2 | 12/2002 | Madan et al. |
| 6,500,188 B2 | 12/2002 | Harper et al. |
| 6,514,267 B2 | 2/2003 | Jewett |
| 6,537,291 B2 | 3/2003 | Friedman et al. |
| 6,561,983 B2 | 5/2003 | Cronin et al. |
| 6,565,520 B1 | 5/2003 | Young |
| 6,588,277 B2 | 7/2003 | Giordano et al. |
| 6,589,200 B1 | 7/2003 | Schwemberger et al. |
| 6,607,540 B1 | 8/2003 | Shipp |
| 6,623,500 B1 | 9/2003 | Cook et al. |
| 6,626,926 B2 | 9/2003 | Friedman et al. |
| 6,633,234 B2 | 10/2003 | Wiener et al. |
| 6,652,539 B2 | 11/2003 | Shipp et al. |
| 6,652,545 B2 | 11/2003 | Shipp et al. |
| 6,660,017 B2 | 12/2003 | Beaupre |
| 6,662,127 B2 | 12/2003 | Wiener et al. |
| 6,666,875 B1 | 12/2003 | Sakurai et al. |
| 6,678,621 B2 | 1/2004 | Wiener et al. |
| 6,679,899 B2 | 1/2004 | Wiener et al. |
| 6,719,776 B2 | 4/2004 | Baxter et al. |
| 6,752,815 B2 | 6/2004 | Beaupre |
| 6,773,444 B2 | 8/2004 | Messerly |
| 6,869,439 B2 | 3/2005 | White et al. |
| 6,908,472 B2 | 6/2005 | Wiener et al. |
| 6,915,623 B2 | 7/2005 | Dey et al. |
| 6,945,981 B2 | 9/2005 | Donofrio et al. |
| 6,976,969 B2 | 12/2005 | Messerly |
| 7,037,306 B2 | 5/2006 | Podany et al. |
| 7,066,895 B2 | 6/2006 | Podany |
| 7,074,218 B2 | 7/2006 | Washington et al. |
| 7,108,695 B2 | 9/2006 | Witt et al. |
| 7,128,720 B2 | 10/2006 | Podany |
| 7,135,030 B2 | 11/2006 | Schwemberger et al. |
| 7,163,548 B2 | 1/2007 | Stulen et al. |
| 7,179,254 B2 | 2/2007 | Pendekanti et al. |
| 7,179,271 B2 | 2/2007 | Friedman et al. |
| 7,207,997 B2 | 4/2007 | Shipp et al. |
| 7,217,128 B2 | 5/2007 | Atkin et al. |
| 7,217,893 B1 | 5/2007 | Huang et al. |
| 7,230,199 B2 | 6/2007 | Chou et al. |
| 7,244,262 B2 | 7/2007 | Wiener et al. |
| 7,269,873 B2 | 9/2007 | Brewer et al. |
| 7,273,483 B2 | 9/2007 | Wiener et al. |
| 7,300,446 B2 | 11/2007 | Beaupre |
| 7,335,997 B2 | 2/2008 | Wiener |
| 7,337,010 B2 | 2/2008 | Howard et al. |
| 7,977,587 B2 | 7/2011 | Rajagopal et al. |
| 8,435,258 B2 | 5/2013 | Young et al. |
| 8,672,959 B2 | 3/2014 | Witt et al. |
| 10,368,898 B2 | 8/2019 | Brown et al. |
| 10,499,917 B2 * | 12/2019 | Scheib ............ A61B 17/07207 |
| 2001/0048855 A1 | 12/2001 | Lin |
| 2002/0002379 A1 | 1/2002 | Bishop |
| 2002/0026184 A1 | 2/2002 | Witt et al. |
| 2002/0077645 A1 | 6/2002 | Wiener et al. |
| 2002/0091339 A1 | 7/2002 | Horzewski et al. |
| 2003/0144680 A1 | 7/2003 | Kellogg et al. |
| 2003/0149424 A1 | 8/2003 | Barlev et al. |
| 2003/0199794 A1 | 10/2003 | Sakurai et al. |
| 2003/0212363 A1 | 11/2003 | Shipp |
| 2003/0216732 A1 | 11/2003 | Truckai et al. |
| 2004/0097972 A1 | 5/2004 | Shipp et al. |
| 2004/0116952 A1 | 6/2004 | Sakurai et al. |
| 2004/0256487 A1 | 12/2004 | Collins et al. |
| 2005/0091770 A1 | 5/2005 | Mourad et al. |
| 2005/0107658 A1 | 5/2005 | Brockway |
| 2005/0113815 A1 | 5/2005 | Ritchie et al. |
| 2005/0119677 A1 | 6/2005 | Shipp |
| 2005/0149063 A1 | 7/2005 | Young et al. |
| 2005/0203329 A1 | 9/2005 | Muto et al. |
| 2005/0234338 A1 | 10/2005 | Masuda |
| 2005/0234484 A1 | 10/2005 | Houser et al. |
| 2006/0058825 A1 | 3/2006 | Ogura et al. |
| 2006/0079878 A1 | 4/2006 | Houser |
| 2006/0079879 A1 * | 4/2006 | Faller ............ A61B 17/320092 606/40 |
| 2006/0087286 A1 | 4/2006 | Phillips et al. |
| 2006/0129168 A1 | 6/2006 | Shipp |
| 2006/0178579 A1 | 8/2006 | Haynes |
| 2006/0178667 A1 | 8/2006 | Sartor et al. |
| 2006/0194567 A1 | 8/2006 | Kelly et al. |
| 2006/0206100 A1 | 9/2006 | Eskridge et al. |
| 2006/0217729 A1 | 9/2006 | Eskridge et al. |
| 2007/0011836 A1 | 1/2007 | Brewer et al. |
| 2007/0149881 A1 | 6/2007 | Rabin |
| 2007/0166663 A1 | 7/2007 | Telles et al. |
| 2007/0175960 A1 | 8/2007 | Shelton et al. |
| 2007/0227866 A1 | 10/2007 | Dimig |
| 2007/0239028 A1 | 10/2007 | Houser et al. |
| 2007/0239101 A1 | 10/2007 | Kellogg |
| 2007/0282332 A1 | 12/2007 | Witt et al. |
| 2007/0282333 A1 | 12/2007 | Fortson et al. |
| 2008/0033248 A1 | 2/2008 | Akagi |
| 2008/0051693 A1 | 2/2008 | Babaev |
| 2008/0245841 A1 | 10/2008 | Smith et al. |
| 2009/0138006 A1 | 5/2009 | Bales et al. |

(56) References Cited

U.S. PATENT DOCUMENTS

| | | |
|---|---|---|
| 2009/0143797 A1 | 6/2009 | Smith et al. |
| 2009/0143805 A1 | 6/2009 | Palmer et al. |
| 2009/0223033 A1 | 9/2009 | Houser |
| 2010/0004669 A1 | 1/2010 | Smith et al. |
| 2010/0090420 A1 | 4/2010 | Nickels, Jr. et al. |
| 2012/0078278 A1 | 3/2012 | Bales, Jr. et al. |
| 2012/0215220 A1* | 8/2012 | Manzo ............... A61B 34/30 |
| | | 606/46 |
| 2013/0338691 A1 | 12/2013 | Young et al. |
| 2014/0107684 A1 | 4/2014 | Craig |
| 2015/0148830 A1 | 5/2015 | Stulen et al. |
| 2015/0245850 A1 | 9/2015 | Hibner et al. |
| 2017/0354433 A1* | 12/2017 | Nickson ......... A61B 17/320036 |
| 2018/0049829 A1* | 2/2018 | Yates .............. A61B 17/07207 |
| 2018/0078268 A1* | 3/2018 | Messerly ....... A61B 17/320092 |
| 2019/0201020 A1 | 7/2019 | Shelton, IV et al. |

* cited by examiner

SURGICAL SYSTEM INCLUDING BLADE VISUALIZATION MARKINGS

FIELD

The present disclosure relates to energy-based surgical systems and instruments and, more particularly, to surgical systems and instruments including blade visualization markings.

BACKGROUND

Surgical instruments and systems incorporating ultrasonic functionality utilize ultrasonic energy, i.e., ultrasonic vibrations, to treat tissue. More specifically, mechanical vibration energy transmitted at ultrasonic frequencies can be utilized to treat, e.g., seal and transect, tissue. A surgical instrument incorporating ultrasonic functionality may include, for example, an ultrasonic blade and a clamp mechanism to enable clamping of tissue against the blade. Ultrasonic energy transmitted to the blade causes the blade to vibrate at very high frequencies, which allows for heating tissue to treat tissue clamped against or otherwise in contact with the blade.

SUMMARY

Provided in accordance with aspects of the disclosure is a surgical system including an elongated assembly and an end effector supported by the elongated assembly. The end effector includes a blade and a jaw member movable relative to the blade between a spaced-apart position and an approximated position for clamping tissue. The blade defines a first width and the jaw member defines a second width wider than the first width. The jaw member defines a first side facing the blade and a second side facing away from the blade. A marking is formed on the second side of the jaw member facing away from the blade. The marking defines a third width substantially equal to the first width of the blade to allow a surgeon to visualize a width of the blade when the blade is not visible.

According to aspects of the disclosure, the blade and the jaw member each define a curved profile. The marking defines a curved profile corresponding with the curved profile of the blade.

According to aspects of the disclosure, the marking includes an etching or an engraving formed on the second side of the jaw member facing away from the blade. The etching or making may be laser etched on the jaw member.

According to aspects of the disclosure, the marking includes a set of at least two dashed lines extending along the blade.

According to aspects of the disclosure, a central axis is defined by the jaw member. The blade extends along the central axis of the jaw member. The marking extends along the central axis of the jaw member.

According to aspects of the disclosure, the blade is configured to transmit ultrasonic energy to the tissue.

BRIEF DESCRIPTION OF THE DRAWINGS

The above and other aspects and features of the present disclosure will become more apparent in light of the following detailed description when taken in conjunction with the accompanying drawings.

DETAILED DESCRIPTION

Figure 1:
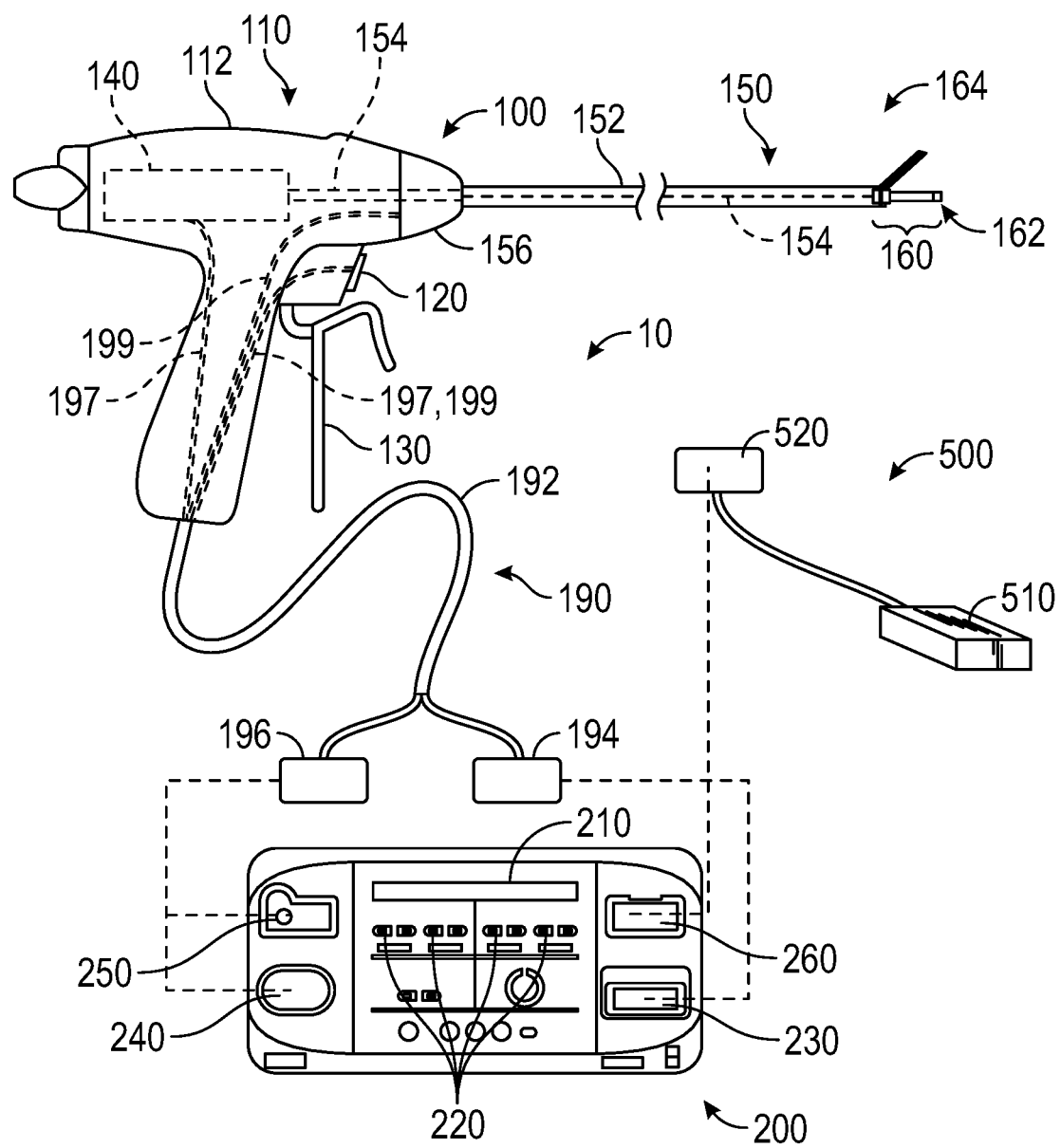
FIG. 1 is a side view of a surgical system provided in accordance with the present disclosure including a surgical instrument, a surgical generator, and a return electrode device.

As used herein, the term "distal" refers to the portion that is being described which is further from an operator (whether a human surgeon or a surgical robot), while the term "proximal" refers to the portion that is being described which is closer to an operator. Further, to the extent consistent, any of the aspects and features detailed herein may be used in conjunction with any or all of the other aspects and features detailed herein.

Descriptions of technical features or aspects of an exemplary configuration of the disclosure should typically be considered as available and applicable to other similar features or aspects in another exemplary configuration of the disclosure. Accordingly, technical features described herein according to one exemplary configuration of the disclosure may be applicable to other exemplary configurations of the disclosure, and thus duplicative descriptions may be omitted herein.

Exemplary configurations of the disclosure will be described more fully below (e.g., with reference to the accompanying drawings). Like reference numerals may refer to like elements throughout the specification and drawings.

During surgical procedures, when a surgeon is employing an end effector having a jaw member and a blade, the blade is often facing away from the surgeon and/or is obstructed by the jaw member, tissue, other instrumentation, etc. Therefore, the blade is not directly visible to the surgeon and an amount of tissue being grasped is not immediately clear to the surgeon. This is particularly true when the jaw member has a wider width than the blade. As described herein, applying a marking having a same width as a width of the blade to a side of the jaw member facing away from the blade can provide an easily observable visual cue for a surgeon to visualize the location of the blade and, thus, how much tissue is in contact with the blade, even when the blade itself is not directly visible.

Referring to FIG. 1, a surgical system provided in accordance with aspects of the present disclosure is shown generally identified by reference numeral 10 including a surgical instrument 100, a surgical generator 200, and, in some aspects, a return electrode device 500, e.g., including a return pad 510. Surgical instrument 100 includes a handle assembly 110, an elongated assembly 150 extending distally from handle assembly 110, an end effector assembly 160 disposed at a distal end of elongated assembly 150, and a cable assembly 190 operably coupled with handle assembly 110 and extending therefrom for connection to surgical generator 200.

Surgical generator 200 includes a display 210, a plurality user interface features 220, e.g., buttons, touch screens, switches, etc., an ultrasonic plug port 230, a bipolar electrosurgical plug port 240, and active and return monopolar electrosurgical plug ports 250, 260, respectively. As an alternative to plural dedicated ports 230-260, one or more common ports (not shown) may be configured to act as any two or more of ports 230-260.

Surgical instrument 100 may be configured to operate in one or more electrosurgical modes supplying Radio Frequency (RF) energy to tissue to treat tissue, e.g., a monopolar configuration and/or a bipolar configuration, and/or in an ultrasonic mode supplying ultrasonic energy to tissue to treat tissue. The modes may operate simultaneously, sequentially, or in any other suitable manner. Surgical generator 200 is configured to produce ultrasonic drive signals for output through ultrasonic plug port 230 to surgical instrument 100 to activate surgical instrument 100 in the ultrasonic mode and to provide electrosurgical energy, e.g., RF bipolar energy for output through bipolar electrosurgical plug port 240 and/or RF monopolar energy for output through active monopolar electrosurgical port 250 to surgical instrument 100 to activate surgical instrument 100 in the one or more electrosurgical modes. Plug 520 of return electrode device 500 is configured to connect to return monopolar electrosurgical plug port 260 to return monopolar electrosurgical energy from surgical instrument 100 in the monopolar electrosurgical mode. In other aspects, the electrosurgical functionality (and associated components and configurations) of surgical instrument 100 may be omitted such that surgical instrument 100 operates only in an ultrasonic mode.

Continuing with reference to FIG. 1, handle assembly 110 includes a housing 112, an activation button 120, and a clamp trigger 130. Housing 112 is configured to support an ultrasonic transducer 140. Ultrasonic transducer 140 may be permanently engaged within housing 112 or removable therefrom. Ultrasonic transducer 140 includes a piezoelectric stack or other suitable ultrasonic transducer components electrically coupled to surgical generator 200, e.g., via one or more of first electrical lead wires 197, to enable communication of ultrasonic drive signals to ultrasonic transducer 140 to drive ultrasonic transducer 140 to produce ultrasonic vibration energy that is transmitted along a waveguide 154 of elongated assembly 150 to blade 162 of end effector assembly 160 of elongated assembly 150, as detailed below. Feedback and/or control signals may likewise be communicated between ultrasonic transducer 140 and surgical generator 200. Ultrasonic transducer 140, more specifically, and as detailed below, may include a stack of piezoelectric elements secured, under pre-compression between proximal and distal end masses or a proximal end mass and an ultrasonic horn with first and second electrodes electrically coupled between piezoelectric elements of the stack of piezoelectric elements to enable energization thereof to produce ultrasonic energy. However, other suitable ultrasonic transducer configurations, including plural transducers and/or non-longitudinal, e.g., torsional, transducers are also contemplated.

An activation button 120 is disposed on housing 112 and coupled to or between ultrasonic transducer 140 and/or surgical generator 200, e.g., via one or more of first electrical lead wires 197, to enable activation of ultrasonic transducer 140 in response to depression of activation button 120. In some configurations, activation button 120 may include an ON/OFF switch. In other configurations, activation button 120 may include multiple actuation switches to enable activation from an OFF position to different actuated positions corresponding to different activation settings, e.g., a first actuated position corresponding to a first activation setting (such as a LOW power or tissue sealing setting) and a second actuated position corresponding to a second activation setting (such as a HIGH power or tissue transection setting). In still other configurations, separate activation buttons may be provided, e.g., a first actuation button for activating a first activation setting and a second activation button for activating a second activation setting. Additional activation buttons, sliders, wheels, etc. are also contemplated to enable control of various different activation settings from housing 112.

Elongated assembly 150 of surgical instrument 100 includes an outer drive sleeve 152, a waveguide 154, a rotation knob 156, and an end effector assembly 160 including a blade 162 and a jaw member 164. Rotation knob 156 is rotatable in either direction to rotate elongated assembly 150 in either direction relative to handle assembly 110. The drive assembly operably couples a proximal portion of outer drive sleeve 152 to clamp trigger 130 of handle assembly 110. A distal portion of outer drive sleeve 152 is operably coupled to jaw member 164. Advancing the outer drive sleeve 152 actuates the jaw member 164 between open and clamped configurations. Other suitable drive structures as opposed to a sleeve are also contemplated such as, for example, drive rods, drive cables, drive screws, etc.

Referring still to FIG. 1, the drive assembly may be tuned to provide a jaw clamping force, or jaw clamping force within a jaw clamping force range, to tissue clamped between jaw member 164 and blade 162 or may include a force limiting feature whereby the clamping force applied to tissue clamped between jaw member 164 and blade 162 is limited to a particular jaw clamping force or a jaw clamping force within a jaw clamping force range.

Waveguide 154 includes blade 162 disposed at a distal end thereof. Blade 162 may be integrally formed with waveguide 154, separately formed and subsequently attached (permanently or removably) to waveguide 154, or otherwise operably coupled with waveguide 154. Waveguide 154 and/or blade 162 may be formed from titanium, a titanium alloy, or other suitable electrically conductive material(s), although non-conductive materials are also contemplated. Waveguide 154 includes a proximal connector (not shown), e.g., a threaded male connector, configured for engagement, e.g., threaded engagement within a threaded female receiver, of ultrasonic transducer 140 such that ultrasonic motion produced by ultrasonic transducer 140 is transmitted along waveguide 154 to blade 162 for treating tissue clamped between blade 162 and jaw member 164 or positioned adjacent to blade 162.

Cable assembly 190 of surgical instrument 100 includes a cable 192, an ultrasonic plug 194, and an electrosurgical plug 196. Ultrasonic plug 194 is configured for connection with ultrasonic plug port 230 of surgical generator 200 while electrosurgical plug 196 is configured for connection with bipolar electrosurgical plug port 240 of surgical generator 200 and/or active monopolar electrosurgical plug port 250 of surgical generator 200. In configurations where generator 200 includes a common port, cable assembly 190 may include a common plug (not shown) configured to act as both the ultrasonic plug 194 and the electrosurgical plug 196. In configurations where surgical instrument 100 is only configured for ultrasonic operation, electrosurgical plug 196 and associated components are omitted.

Plural first electrical lead wires 197 electrically coupled to ultrasonic plug 194 extend through cable 192 and into handle assembly 110 for electrical connection to ultrasonic transducer 140 and/or activation button 120 to enable the selective supply of ultrasonic drive signals from surgical generator 200 to ultrasonic transducer 140 upon activation of activation button 120 in an ultrasonic mode. In addition, and where electrosurgical functionality is provided, plural second electrical lead wires 199 are electrically coupled to electrosurgical plug 196 and extend through cable 192 into handle assembly 110. In bipolar configurations, separate second electrical lead wires 199 are electrically coupled to waveguide 154 and jaw member 164 (and/or different portions of jaw member 164) such that bipolar electrosurgical energy may be conducted between blade 162 and jaw member 164 (and/or between different portions of jaw member 164). In monopolar configurations, a second electrical lead wire 199 is electrically coupled to waveguide 154 such that monopolar electrosurgical energy may be supplied to tissue from blade 162. Alternatively, or additionally, a second electrical lead wire 199 may electrically couple to jaw member 164 in the monopolar configuration to enable monopolar electrosurgical energy to be supplied to tissue from jaw member 164. In configurations where both bipolar and monopolar functionality are enabled, one or more of the second electrical lead wires 199 may be used for both the delivery of bipolar energy and monopolar energy; alternatively, bipolar and monopolar energy delivery may be provided by separate second electrical lead wires 199. One or more other second electrical lead wires 199 is electrically coupled to activation button 120 to enable the selective supply of electrosurgical energy from surgical generator 200 to waveguide 154 and/or jaw member 164 upon activation of activation button 120 in an electrosurgical mode.

Figure 2:
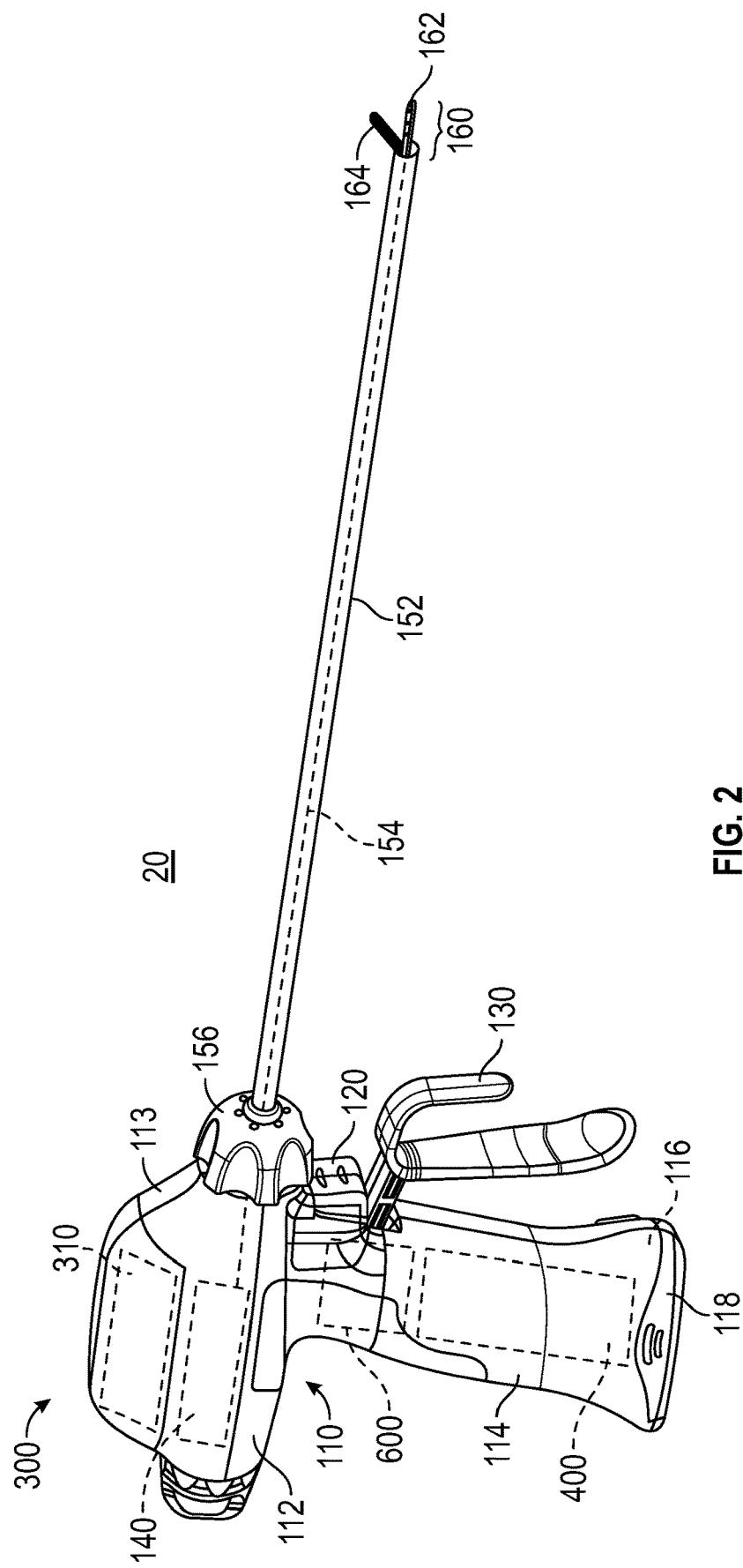
FIG. 2 is a perspective view of another surgical system provided in accordance with the present disclosure including a surgical instrument incorporating an ultrasonic generator, electrosurgical generator, and power source therein.

As an alternative to a remote generator 200, surgical system 10 may be at least partially cordless in that it incorporates an ultrasonic generator, an electrosurgical generator, and/or a power source, e.g., a battery, thereon or therein. In this manner, the connections from surgical instrument 100 to external devices, e.g., generator(s) and/or power source(s), is reduced or eliminated. More specifically, with reference to FIG. 2, another surgical system in accordance with the present disclosure is shown illustrated as a surgical instrument 20 supporting an ultrasonic generator 310, a power source (e.g., battery assembly 400), and an electrosurgical generator 600 thereon or therein. Surgical instrument 20 is similar to surgical instrument 100 (FIG. 1) and may include any of the features thereof except as explicitly contradicted below. Accordingly, only differences between surgical instrument 20 and surgical instrument 100 (FIG. 1) are described in detail below while similarities are omitted or summarily described.

Housing 112 of surgical instrument 20 includes a body portion 113 and a fixed handle portion 114 depending from body portion 113. Body portion 113 of housing 112 is configured to support an ultrasonic transducer and generator assembly ("TAG") 300 including ultrasonic generator 310 and ultrasonic transducer 140. TAG 300 may be permanently engaged with body portion 113 of housing 112 or removable therefrom.

Fixed handle portion 114 of housing 112 defines a compartment 116 configured to receive battery assembly 400 and electrosurgical generator 600 and a door 118 configured to enclose compartment 116. An electrical connection assembly (not shown) is disposed within housing 112 and serves to electrically couple activation button 120, ultrasonic generator 310 of TAG 300, and battery assembly 400 with one another when TAG 300 is supported on or in body portion 113 of housing 112 and battery assembly 400 is disposed within compartment 116 of fixed handle portion 114 of housing 112, thus enabling activation of surgical instrument 20 in an ultrasonic mode in response to appropriate actuation of activation button 120. Further, the electrical connection assembly or a different electrical connection assembly disposed within housing 112 serves to electrically couple activation button 120, electrosurgical generator 600, battery assembly 400, and end effector assembly 160 (e.g., blade 162 and jaw member 164 and/or different portions of jaw member 164) with one another when electrosurgical generator 600 and battery assembly 400 are disposed within compartment 116 of fixed handle portion 114 of housing 112, thus enabling activation of surgical instrument 20 in an electrosurgical mode, e.g., bipolar RF, in response to appropriate actuation of activation button 120. For a monopolar electrosurgical mode, return electrode device 500 (FIG. 1) may be configured to connect to surgical instrument 20 (electrosurgical generator 600 thereof, more specifically), to complete a monopolar circuit through tissue and between surgical instrument 30 (e.g., blade 162 and/or jaw member 164) and return electrode device 500 (FIG. 1).

Unless otherwise indicated below, the end effectors 360, 460 and 560 described below are substantially the same as the end effector 160 described above with reference to FIGS. 1 and 2, and thus duplicative descriptions may be omitted below. Further, end effectors 360, 460, 560 may be utilized with any of the surgical systems detailed above or any other suitable surgical systems.

Figure 3:
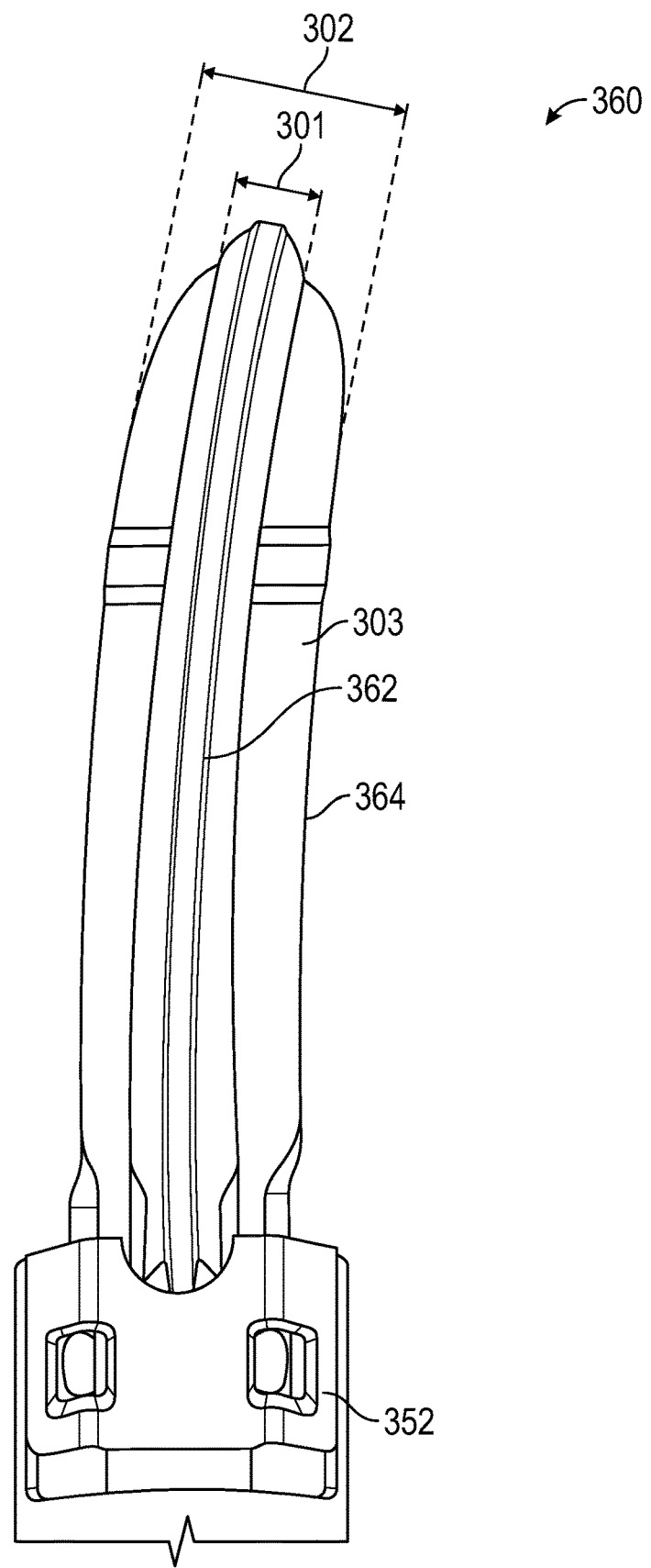
FIG. 3 is a bottom-up view of a blade and a jaw member of an end effector assembly of a surgical system in accordance with the present disclosure.

With reference to FIG. 3, a surgical system including an elongated assembly 352 and an end effector 360 supported by the elongated assembly 352. The end effector 360 includes a blade 362 and a jaw member 364 movable relative to the blade 362 between a spaced-apart position and an approximated position for clamping tissue. The blade 362 defines a first width 301 and the jaw member 364 defines a second width 302 that is wider than the first width 301. The jaw member 364 defines a first side 303 facing the blade 362 and a second side (not shown in FIG. 3—see second side 404 shown in FIG. 4) facing away from the blade 362. It is noted that where blade 362 defines a tapered configuration or otherwise variable width along its length, the width of the markings described herein (e.g., markings 401 or 501) may correspond to the maximum width, the minimum width, or an average width of the blade 362.

The blade 362 and the jaw member 364 may each define a curved profile. When the blade 362 and the jaw member 364 each define a curved profile the marking (see, e.g., markings 401 or 501 described with reference to FIG. 4 or 5, respectively) define a curved profile corresponding with the curved profile of the blade 362. Likewise, where blade 362 defines a tapered configuration or otherwise variable width along its length, the marking (see, e.g., markings 401 or 501 described with reference to FIG. 4 or 5, respectively) may match the shape of the blade, may corresponding to the maximum width, may corresponding to the minimum width, or may corresponding to an average width.

The blade 362 is configured to transmit ultrasonic energy to the tissue.

Figure 4:
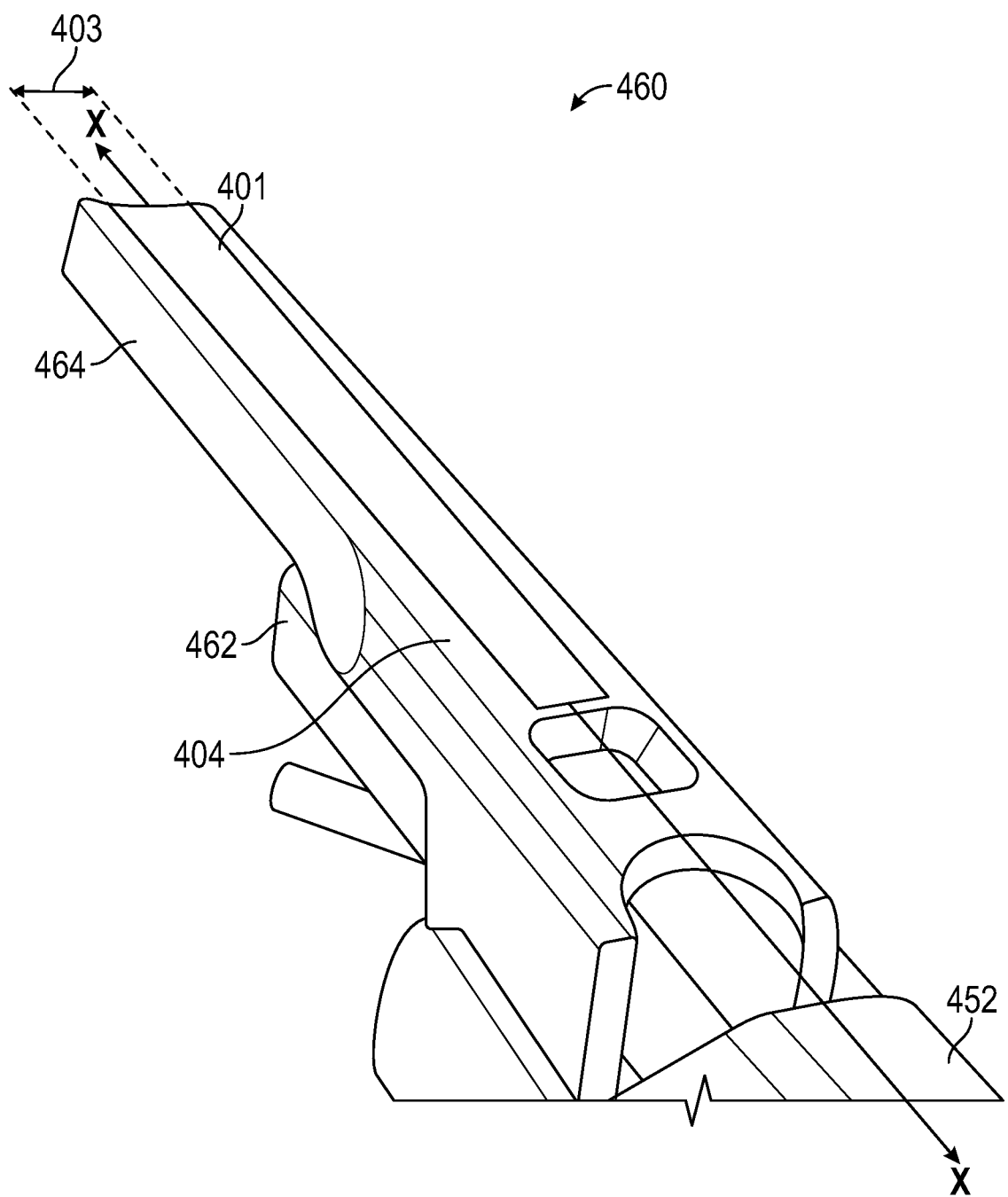
FIG. 4 is a perspective view of a jaw member of an end effector assembly of a surgical system including markings for visualizing a width of a blade in accordance with the present disclosure.

Referring to FIG. 4, in end effector 460 supported by elongated assembly 452 a marking 401 is formed on the second side 404 of the jaw member 464 facing away from the blade 462. The marking 401 defines a third width 403 substantially equal to the first width of the blade 462 to allow a surgeon to visualize a width of the blade 462 when the blade 462 is not visible.

A central axis X-X is defined by the jaw member 464. The blade 462 extends along the central axis X-X of the jaw member 464. The marking 401 also extends along the central axis X-X of the jaw member 464. As an example, the marking 401 may be applied as a paint, resin, or any other suitable indicator on the second side 404 of the jaw member 464. Where the blade deviates from the central axis X-X or defines another configuration, the marking 401 may similarly deviate or otherwise follow the configuration of the blade.

Figure 5:
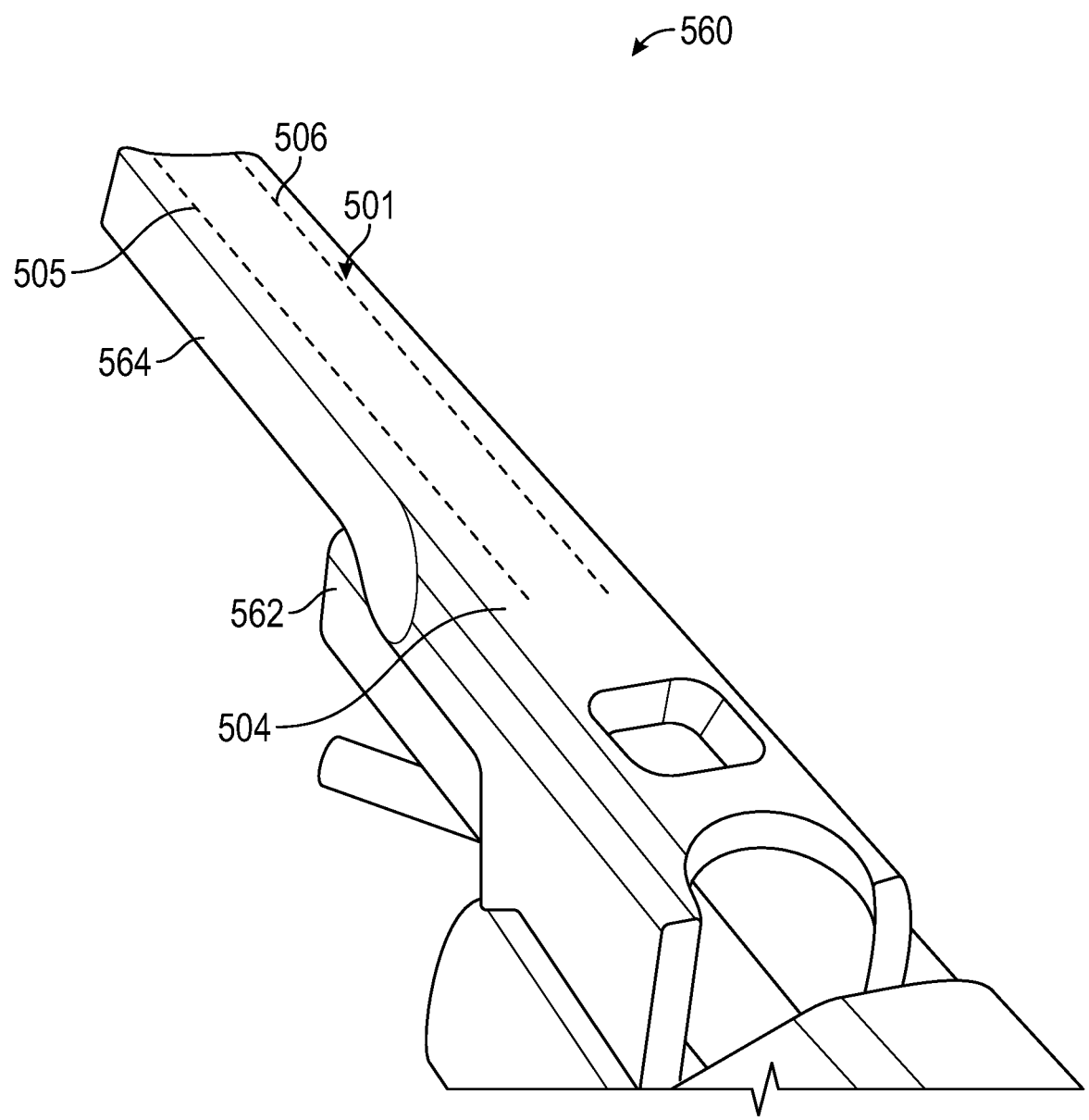
FIG. 5 is a perspective view of a jaw member of an end effector assembly of a surgical system including other markings for visualizing a width of a blade in accordance with the present disclosure.

Referring to FIG. 5, in end effector assembly 560, the marking 501 includes an etching or an engraving formed on the second side 504 of the jaw member 564 facing away from the blade 562. The etching or engraving may be laser etched into the jaw member 464 through a portion or the entire thickness thereof.

The marking 501 may alternatively or additionally include a set of at least two dashed lines 505, 506 extending along the blade 564. The dashed lines 505, 506 may be applied as paint or resin, or may be laser etched into the jaw member 464.

The markings described herein may be raised structures, may be formed as continuous channels or slots, or may be formed as a series of longitudinally spaced parts channels or slots (e.g. appearing as dashed lines) arranged along a jaw member, as described herein.

Figure 6:
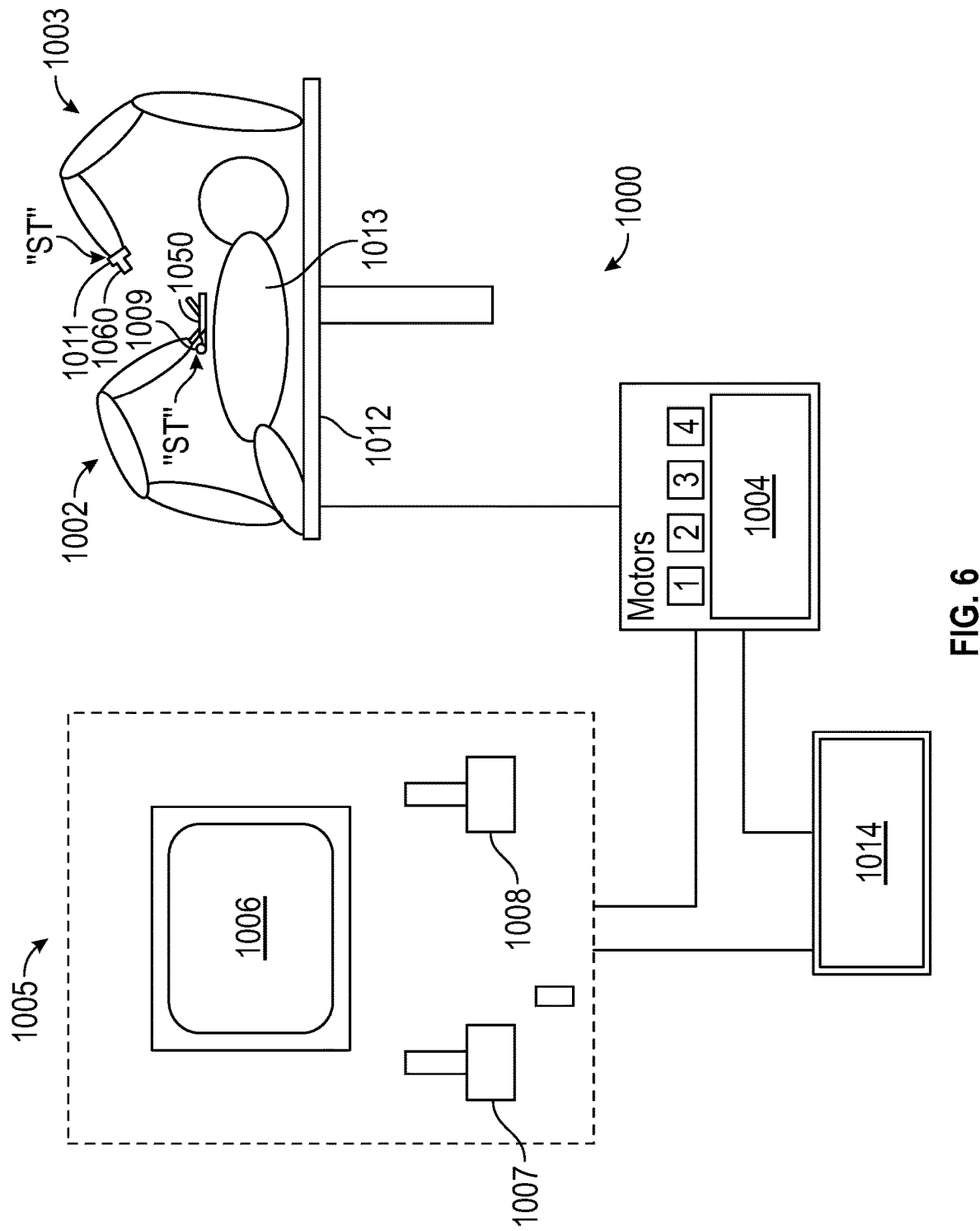
FIG. 6 is a schematic illustration of a robotic surgical system provided in accordance with the present disclosure.

Referring to FIG. 6, a robotic surgical system in accordance with the aspects and features of the present disclosure is shown generally identified by reference numeral 1000. For the purposes herein, robotic surgical system 1000 is generally described. Aspects and features of robotic surgical system 1000 not germane to the understanding of the present disclosure are omitted to avoid obscuring the aspects and features of the present disclosure in unnecessary detail.

Robotic surgical system 1000 generally includes a plurality of robot arms 1002, 1003; a control device 1004; and an operating console 1005 coupled with control device 1004. Operating console 1005 may include a display device 1006, which may be set up in particular to display three dimensional images; and manual input devices 1007, 1008, by means of which a person (not shown), for example a surgeon, may be able to telemanipulate robot arms 1002, 1003 in a first operating mode. Robotic surgical system 1000 may be configured for use on a patient 1013 lying on a patient table 1012 to be treated in a minimally invasive manner. Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and an attaching device 1009, 1011, to which may be attached, for example, a surgical tool "ST" supporting an end effector 1050, 1060. One of the surgical tools "ST" may be surgical instrument 100 (FIG. 1), surgical instrument 20 (FIG. 2), or the surgical system described with reference to FIG. 3 or FIG. 4 herein. In such configurations, robotic surgical system 1000 may include or be configured to connect to an ultrasonic generator, an electrosurgical generator, and/or a power source. The other surgical tool "ST" may include any other suitable surgical instrument, e.g., an endoscopic camera, other surgical tool, etc. Robot arms 1002, 1003 may be driven by electric drives, e.g., motors, that are connected to control device 1004. Control device 1004 (e.g., a computer) may be configured to activate the motors, in particular by means of a computer program, in such a way that robot arms 1002, 1003, their attaching devices 1009, 1011, and, thus, the surgical tools "ST" execute a desired movement and/or function according to a corresponding input from manual input devices 1007, 1008, respectively. Control device 1004 may also be configured in such a way that it regulates the movement of robot arms 1002, 1003 and/or of the motors.

While several aspects of the disclosure have been detailed above and are shown in the drawings, it is not intended that the disclosure be limited thereto, as it is intended that the disclosure be as broad in scope as the art will allow and that the specification be read likewise. Therefore, the above description and accompanying drawings should not be construed as limiting, but merely as exemplifications of particular aspects. Those skilled in the art will envision other modifications within the scope and spirit of the claims appended hereto.

What is claimed is:

1. A surgical system, comprising:
   an elongated assembly;
   an end effector supported by the elongated assembly, the end effector including a blade and a jaw member movable relative to the blade between a spaced-apart position and an approximated position for clamping tissue therebetween, the blade defining a first width, the jaw member defining a second width wider than the first width, a first side facing the blade, and a second side facing away from the blade; and
   at least one marking formed on the second side of the jaw member facing away from the blade, the at least one marking defining a third width substantially equal to the first width of the blade.

2. The surgical system of claim 1, wherein the blade and the jaw member each define a curved profile, and wherein the at least one marking defines a curved profile corresponding with the curved profile of the blade.

3. The surgical system of claim 1, wherein the at least one marking includes at least one etching or at least one engraving formed on the second side of the jaw member facing away from the blade.

4. The surgical system of claim 3, wherein the at least one etching or the at least one engraving is a laser etched on the second side of the jaw member facing away from the blade.

5. The surgical system of claim 1, wherein the at least one marking includes a set of at least two dashed lines.

6. The surgical system of claim 1, further including a central axis defined by the jaw member, wherein the blade extends along the central axis of the jaw member, and wherein the at least one marking extends along the central axis of the jaw member.

7. The surgical system of claim 1, wherein the blade is configured to transmit ultrasonic energy to the tissue.

8. An end effector assembly of a surgical system, comprising:
   a blade defining a first width;
   a jaw member movable relative to the blade between a spaced-apart position and an approximated position for clamping tissue between the blade and the jaw member, the jaw member defining a second width wider than the first width, a first side facing the blade, and a second side facing away from the blade; and
   at least one marking formed on the second side of the jaw member facing away from the blade, the at least one marking defining a third width substantially equal to the first width of the blade.

9. The end effector assembly of claim 8, wherein the blade and the jaw member each define a curved profile, and wherein the at least one marking defines a curved profile corresponding with the curved profile of the blade.

10. The end effector assembly of claim 8, wherein the at least one marking includes at least one etching or at least one engraving formed on the second side of the jaw member facing away from the blade.

11. The end effector assembly of claim 10, wherein the at least one etching or the at least one engraving is a laser etched on the second side of the jaw member facing away from the blade.

12. The end effector assembly of claim 8, wherein the at least one marking includes a set of at least two dashed lines.

13. The end effector assembly of claim 8, further including a central axis defined by the jaw member, wherein the blade extends along the central axis of the jaw member, and wherein the at least one marking extends along the central axis of the jaw member.

14. The end effector assembly of claim 8, wherein the blade is configured to transmit ultrasonic energy to the tissue.

\* \* \* \* \*